(12) United States Patent
Pahls et al.

(10) Patent No.: US 10,206,804 B1
(45) Date of Patent: Feb. 19, 2019

(54) GLOBAL OSTEOARTHRITIS KNEE BRACE

(71) Applicant: WEBER ORTHOPEDIC INC., Santa Paula, CA (US)

(72) Inventors: Dan Pahls, Honesdale, PA (US); Martha Ortega, Oxnard, CA (US); John Hely, Roanoke, TX (US); David Cormier, Oxnard, CA (US)

(73) Assignee: Weber Orthopedic, L.P., Santa Paula, CA (US)

( * ) Notice: Subject to any disclaimer, the term of this patent is extended or adjusted under 35 U.S.C. 154(b) by 598 days.

(21) Appl. No.: 14/869,946

(22) Filed: Sep. 29, 2015

Related U.S. Application Data

(60) Provisional application No. 62/057,131, filed on Sep. 29, 2014.

(51) Int. Cl.
*A61F 5/01* (2006.01)

(52) U.S. Cl.
CPC .......... *A61F 5/0123* (2013.01); *A61F 5/0109* (2013.01); *A61F 5/0106* (2013.01); *A61F 2005/0137* (2013.01); *A61F 2005/0172* (2013.01); *A61F 2005/0176* (2013.01)

(58) Field of Classification Search
CPC .... A61F 5/0106; A61F 5/0109; A61F 5/0123; A61F 2005/0172; A61F 2005/0174; A61F 2005/0176
USPC ...................................................... 602/16, 26
See application file for complete search history.

(56) References Cited

U.S. PATENT DOCUMENTS

| 4,287,885 | A | * | 9/1981 | Applegate | A61F 13/061 2/24 |
| 5,626,557 | A | * | 5/1997 | Mann | A61F 5/012 602/13 |
| 5,759,167 | A | * | 6/1998 | Shields, Jr. | A61F 5/0106 602/26 |
| 7,201,728 | B2 | | 4/2007 | Sterling | |
| 7,217,249 | B2 | * | 5/2007 | Scott | A61F 5/0109 602/23 |
| 7,862,528 | B2 | * | 1/2011 | Scott | A61F 5/0106 602/23 |
| 7,867,183 | B2 | | 1/2011 | Kazmierczak et al. | |
| 7,963,933 | B2 | | 6/2011 | Nace | |
| 8,333,723 | B2 | | 12/2012 | Hunter et al. | |
| 2012/0157902 | A1 | | 6/2012 | Castillo | |

(Continued)

OTHER PUBLICATIONS

Photograph of 1994 Kinetic Stabilizer using lateral pulls.

*Primary Examiner* — Keri J Nelson
(74) *Attorney, Agent, or Firm* — Paul Y. Feng; One LLP

(57) ABSTRACT

A global osteoarthritis knee brace or orthopedic support includes a flexible, elastic sleeve having a tubular shape with a patella opening at an anterior surface with slits on either side of the opening. The brace includes a first pair of rigid longitudinal stiffeners pivoted therebetween at a hinge that is disposed at the lateral side of the sleeve and likewise at the medial side of the sleeve. The brace further includes an adjustable, flexible patella support having elongated strips at the ends thereof, wherein the patella support is positioned in the interior of the sleeve proximate with the patella opening, where the elongated strips pass from the interior of the sleeve through the slits to the exterior of the sleeve, and extend upward to be adjustably anchored to the sleeve. The wearer pulling on the elongated strips adjusts the patella support.

19 Claims, 3 Drawing Sheets

(56) References Cited

U.S. PATENT DOCUMENTS

2012/0220910 A1* 8/2012 Gaylord ................ A61F 5/0125
602/16
2013/0178772 A1 7/2013 Oaks
2013/0331753 A1* 12/2013 Farrow ................... A61F 5/012
602/16
2015/0290014 A1* 10/2015 Anglada ............... A61F 5/0109
602/26

* cited by examiner

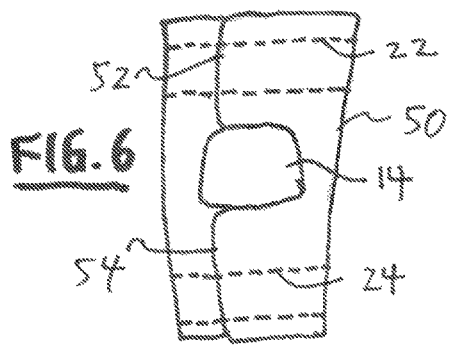
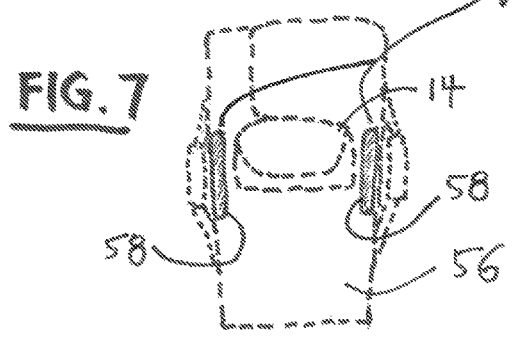
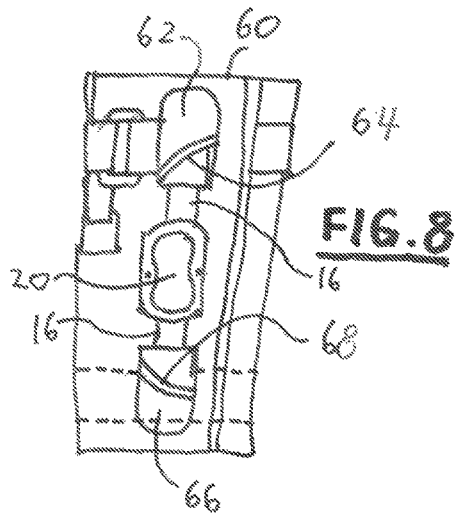
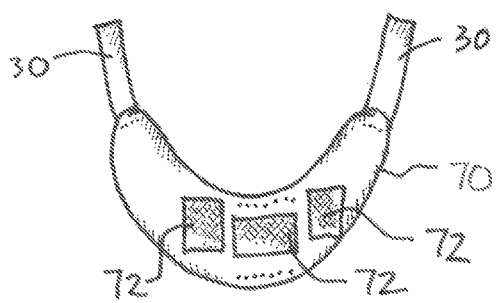

GLOBAL OSTEOARTHRITIS KNEE BRACE

CROSS-REFERENCE TO RELATED APPLICATIONS

This application claims priority to provisional application No. 62/057,131, filed Sep. 29, 2014, by the same inventors, the entire contents of which are incorporated by reference.

FIELD OF THE INVENTION

The present invention relates to an orthopedic brace. In particular, the present invention relates to a global osteoarthritis knee brace.

BACKGROUND

Osteoarthritis is caused by cartilage in a person's knees breaking down over time due to age, accumulated physical strain, etc. The loss of cushioning cartilage in the joint allows bone-on-bone contact, leading to chronic pain. Often, the afflicted knee joint is highly swollen and enlarged. One popular treatment is having the osteoarthritis sufferer wear a knee brace to reduce the knee joint pain and to provide him or her with mobility.

SUMMARY OF THE INVENTION

The present invention in a preferred embodiment is directed to an osteoarthritis knee brace, comprising a flexible and elastic sleeve having a tubular shape with an interior and exterior, lateral and medial surfaces, the sleeve further having a patella opening at an anterior surface, and a plurality of slits on either side of the opening. The brace includes a first pair of rigid longitudinal stiffeners pivoted therebetween at a hinge that is disposed at the lateral surface of the sleeve. A second pair of rigid longitudinal stiffeners pivoted therebetween at a hinge, is disposed at the medial surface of the sleeve. The brace further includes an adjustable, flexible patella support having elongated strips at the ends thereof, wherein the patella support is positioned in the interior of the sleeve proximate with the patella opening, and wherein the elongated strips pass from the interior of the sleeve through the slits to the exterior of the sleeve, and further extend upward to be adjustably anchored to the sleeve, and wherein the wearer pulling on the elongated strips adjusts the patella support. A strap extends circumferentially around the outside of the sleeve. Preferably, the patella support includes a crescent shape and is elastic, and may include padding engaging the patella.

BRIEF DESCRIPTION OF THE DRAWINGS

FIG. 5 is a perspective view of the patella support assembly;

FIG. 6 is an alternative embodiment knee brace with upper and lower openings.

FIG. 7 shows an alternative embodiment knee brace fitted with internal condyle pads.

FIG. 8 shows an alternative embodiment knee brace having pull up pockets instead of loops.

FIG. 9 shows an alternative embodiment patella support.

FIG. 10 is an exemplary embodiment of an internal condyle pad.

DETAILED DESCRIPTION OF THE PREFERRED EMBODIMENTS

Figure 1:
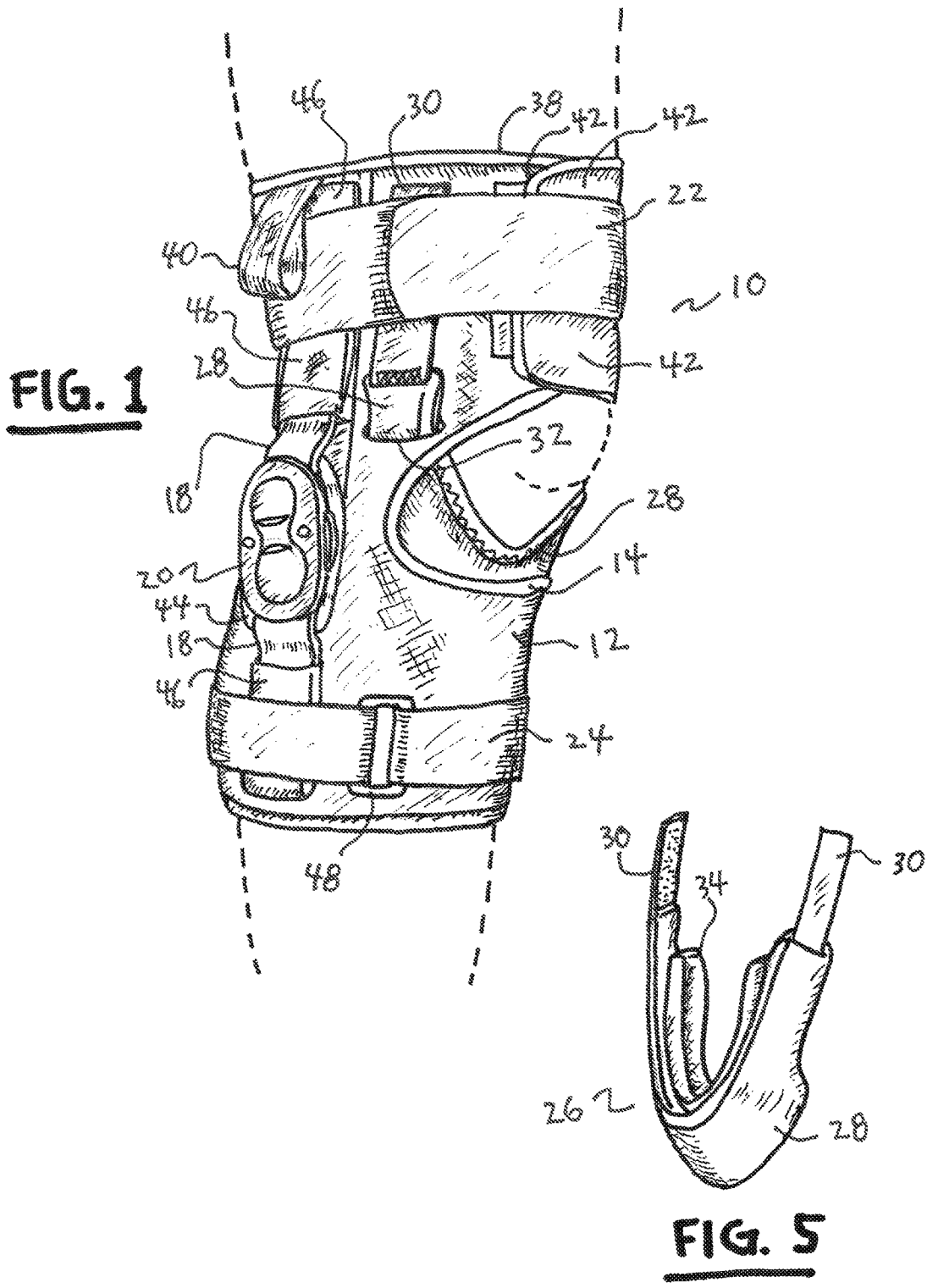
FIG. 1 is a perspective view of the lateral side of a preferred embodiment knee brace as worn on the right leg.

FIG. 1 shows a preferred embodiment of the present invention osteoarthritis knee brace 10 as worn on the right leg of a patient. In this embodiment, the brace 10 is constructed from a tubular-shaped, elastic sleeve or wrap 12 that generally envelopes the knee joint and supports a portion of the upper leg and the lower leg. The sleeve 12 preferably includes a patella opening 14 to expose the patella to minimize skin chafing or wearer discomfort. At the medial and lateral sides of the sleeve 12 are respective stiffeners 16, 18. A hinge 20 is located on each stiffener 16, 18 at about a midpoint so that the stiffeners bend and follow the natural bend of the knee. The stiffeners 16, 18 allow the full flexion and extension range of motion for the knee joint while controlling adduction or abduction knee misalignment. The preferably metal stiffeners 16, 18 are attached to the sleeve 12 and are further retained to the upper and lower leg by use of an optional upper strap 22 and lower strap 24. The straps 22, 24 are preferably inelastic and fitted with hook and loop fasteners (e.g., Velcro®) to provide adjustability to fit the wearer's physique and achieve the desired pressure on the wearer's hamstring and calf.

Fitted inside the sleeve 12 is a generally U-shaped patella control assembly 26, shown in the perspective view of FIG. 5. The patella control assembly 26 preferably includes an adjustable patella sling or support 28 in the shape of a "U" or crescent terminating at opposite ends with attachment/pull strips 30. The U-shaped patella support 28 is preferably made from a stretchable, soft fabric such as neoprene. The pull strips 30 are preferably made from inelastic strips of material that have the hook portion of a hook and loop fastener.

The patella control assembly 26, and specifically the patella support 28, is preferably stitched, glued, welded, or similarly anchored at the base of the "U" to the interior of the sleeve 12 at about the patella opening 14 just beneath the knee joint. The patella support 28 and the sleeve 12 are joined together so that the knee brace 10 when applied by the patient or orthopedist is in one piece without loose parts. Also, the anchoring point ensures the patella support 28 is already positioned generally at the correct location relative to the knee joint without further adjustments. In alternative embodiments, the patella support 28 is not stitched or glued to the sleeve 12 as described above, but rather hangs freely and only from the pull strips 30.

As seen in FIG. 1, the pull strips 30 pass through slit-like openings 32 in the sleeve 12, which slits 32 lead from inside the sleeve to outside the sleeve, where on the outside of the sleeve, the wearer has easy access and can pull upward, at angle, or both, on the pull strips 30 to adjust the force and location of the support 28 against the patella. As described above, the base of the "U" of the patella support 28 is optionally anchored or otherwise stitched to the sleeve 12 near the opening 14 just beneath the knee. So tugging on the pull strips 30 tensions the elastic patella support 28 against the stationary anchor point, and stretches the patella support 28 around the patella for tight support. Once the wearer adjusts the patella support 28 to the desired tension, pressure, and location, she can attach or anchor the pull strips 30 to the exterior of the sleeve 12, which has a pile patch complement to a hook and loop fastener. The openings or slits 32 in the sleeve 12 are wide enough for easy sliding and passage of the pull strips 30. Furthermore, depending on how the individual pull strips 30 are adjusted by the wearer, it is possible that the patella support 28 apply a lateral or medial force component on the knee joint/patella in addition to the upward force. Adjusting the tension in the patella support 28 also adjusts the amount of force or pressure applied against the patella.

The arrangement of the patella control assembly 26 gives the wearer directional force applied to the patella when the wearer pulls on the pull strips 30 that are readily and conveniently accessible from the outside of the sleeve 12. That tension on the patella is maintained when the wearer anchors the pull strips 30 to the exterior of the sleeve 12. If during flexion of the knee the assembly 26 is perceived as uncomfortable or too tight, it is an easy "on the fly" adjustment for the wearer to slightly tension or release the pull strips 30 individually or in unison and re-anchor them to the sleeve 12. This adjustment is independent of the sleeve 12, which remains stationary. Thus, adjustment of the sleeve 12 and the patella support 28 can be achieved independently.

In FIG. 5, the patella control assembly 26 may include an optional, rubber-like patella buttress 34 also having a generally "U," "C," or like shape. The patella buttress 34 is glued, stitched, or fastened to the interior of the patella support 28 and is applied to the patella. The buttress 34 is preferably made from polyurethane, and may be made from felt, an elastomer, gel, or known rubber-like material, to act as a cushion for the wearer's comfort and to help stabilize the patella.

Other shapes for the patella support 28 are contemplated, including a semicircle, a curved strip, a trapezoid, etc., such that their form maximizes engagement and support for the patella. FIG. 9 shows an alternative embodiment patella support 70. It is shaped generally like the U-shape of the patella support 28 shown in FIG. 5, and has the two pull strips 30 that pass through the slits 32 in the sleeve as in the FIG. 5 embodiment. The shape of the patella support 28 is more of a crescent and slightly different from the FIG. 5 embodiment; the shape illustrates an alternative approach to capture or cup the patella.

FIG. 9 shows the interior surface of the patella support 70 that faces the wearer's knee. On that surface facing the knee are nodules, patches, or areas of a tacky material 72 such as silicone or urethane that is silk screened, deposited, or embedded thereon. The tacky material 72 helps the patella support 70 grip the skin of the wearer. The gel patella buttress 34 may thus be omitted.

Figure 2:
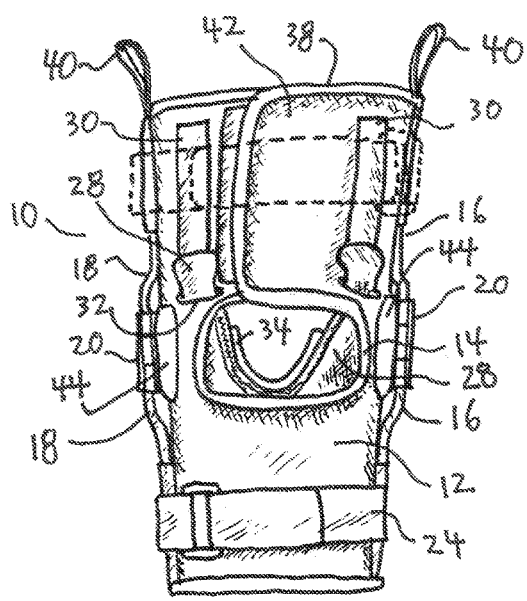
FIG. 2 is a front view of the knee brace from FIG. 1.
Figure 3:
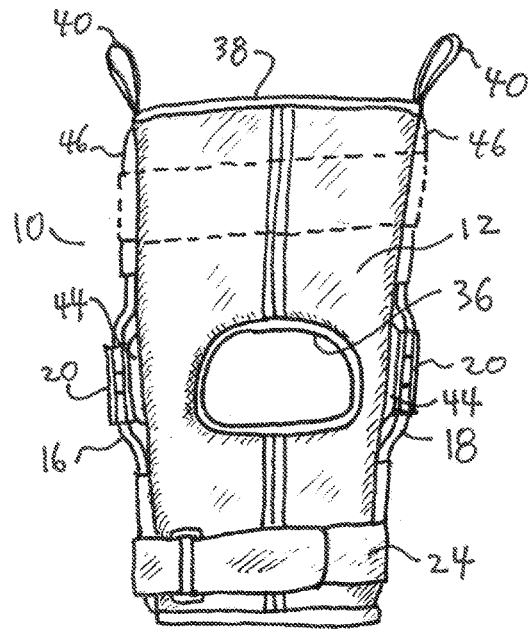
FIG. 3 is rear view of the knee brace from FIG. 1.
Figure 4:
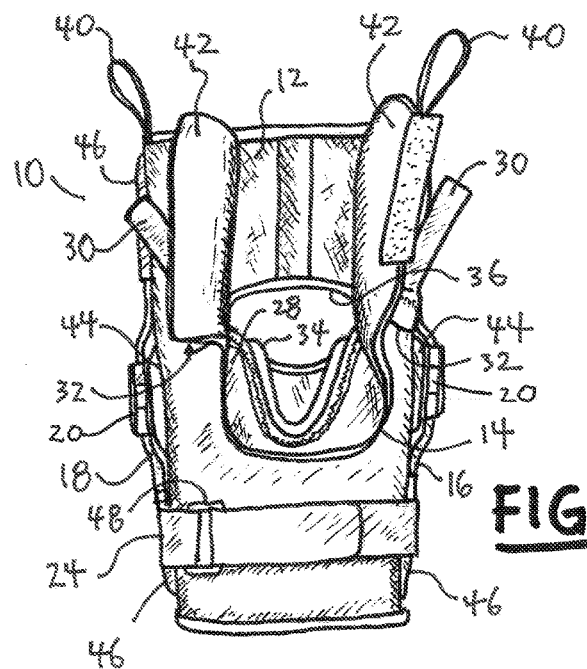
FIG. 4 is a front view of the knee brace with the top anterior portion of the sleeve having the flap closure swung open.

FIGS. 2 and 3 are a front/anterior view and a rear/posterior view, respectively, of the knee brace from FIG. 1. FIG. 4 is a front/anterior view of the sleeve 12 with the flap closure 42 swung open.

As seen in FIGS. 1-4, the sleeve 12 preferably covers the knee joint and portions of the upper and lower leg. The sleeve 12 is preferably made from an elastic, flexible, padded fabric sheet or sheets stitched together. The sheet material includes neoprene, and more preferably, includes an air mesh spacer fabric, which is lighter than neoprene, is more air permeable for wearer comfort, has strength but is stretchable, minimizes moisture and mold build up, etc. The sleeve 12 may be perforated to keep the wearer's leg cool. The exterior may include pile sections to facilitate attachment of the pull strips 30 and other hardware (e.g., straps, flaps) that use hook and loop fasteners.

The sleeve 12 includes the optional patella opening 14 and an optional popliteal or back-of-the-knee opening 36, offering more comfort, minimal bunching of the fabric, and better fitment for the wearer. The interior of the sleeve 12 may include a smooth nylon lining or the like for wearer comfort. The lining minimizes binding if the knee brace 10 is worn over clothing, and feels cool if touching skin.

The top 38 of the sleeve 12 may include optional pull up loops 40 to aid the wearer during application of the knee brace 10 to her limb. Furthermore, to ease the application of the brace, the preferred embodiment sleeve 12 includes upper closure flaps 42 on the anterior portion that swing open, as seen in FIG. 4. This permits easier passage of the wearer's foot and leg into the knee brace 10 when applying the brace, and insures easy removal of the brace 10. The flaps 42 are tensioned, overlap, and close together with hook and loop fasteners. Other closures known in the art are contemplated, including claws, buttons, D-rings, hooks, zippers, laces, straps, etc.

In FIG. 4, the flaps 42 swing apart to reveal the split opening that merges with the patella opening 14 of the sleeve 12. This combined open space creates a wider mouth to receive the wearer's foot and leg for easy passage through the tubular sleeve 12. FIG. 6 is a front elevational view of an alternative embodiment knee brace 50 similar in construction to that shown in FIGS. 1-4, except this embodiment includes optional upper and lower anterior openings 52, 54, above and beneath the patella opening 14. The openings 52, 54 are secured closed using, preferably, hook and loop fasteners. Other means for securing the flaps include zippers, laces, straps, hooks, and the like. The upper and lower straps are shown in dashed lines. The one or more sleeve opening(s) are preferably at the front/anterior, but may be located at the side/medial/lateral or at the back/posterior.

It is further contemplated in an alternative embodiment a knee brace that has an elastic sleeve that is tubular and does not have upper or lower anterior openings. The sleeve would be constructed as a soft, elastic tube. Without the anterior opening(s), no closure flaps are required.

Optional upper and lower straps 22, 24 are used to improve support and attachment of the knee brace 10 to the wearer. The preferred embodiment straps 22, 24 are inelastic, circumscribe the leg, with one end that passes through an optional D-ring 48 to flip over and anchor onto itself via hook and loop fasteners. Of course, more than the two straps 22, 24 shown in the drawings may be used, and one or more may be elastic. In FIGS. 2 and 3, the upper strap 22 is shown in dashed lines to better illustrate the other parts of the knee brace 10. In FIG. 4, the upper strap 22 has been removed for the sake of illustration.

The present invention knee brace 10 includes medial and lateral hinged stiffeners 16, 18. Each stiffener 16, 18 is preferably made of rigid metal or plastic bars that are hinged at about the midpoint. The hinge 20 includes intermeshing gear teeth to enable the bars to pivot. As such, the hinge 20 is polycentric with multiple pivot points to more closely follow the knee joint's natural range of motion. Optional condyle pads 44 may be included at the interior of the hinges 20 to improve wearer comfort. The condyle pads 44 contained soft, resilient padding (e.g., urethane foam, gel, etc.) material to minimize pressure on the medial and lateral sides of the wearer's knee. The stiffeners 16, 18 are positioned inside pockets that are stitched to the sleeve 12. Alternatively, the stiffeners 16, 18 may be embedded into the fabric of the sleeve.

FIG. 7 is a front elevational view of an alternative embodiment knee brace 56 (shown in phantom lines) that is similar to the embodiment shown in FIGS. 1-4, but now includes an internal condyle pad 58 at the medial and lateral locations on either side of the wearer's knee. FIG. 10 provides a more detailed view of one internal condyle pad 58. Each internal condyle pad 58 is oversized and much larger than the external condyle pads 44 shown in FIG. 4. The external condyle pad 58 is preferably a pillow containing air cell, soft gel, Confor®, or like urethane foam. The Confor® foam provides soft padding for the arthritic and swollen knee and is resilient for impact protection. The pillow is covered front and back with a soft fabric and stitched around its periphery, then anchored into the interior of the sleeve by stitching, glue, mechanical fasteners, or the like.

FIG. 8 is a side elevational view of an alternative embodiment knee brace 60 similar to the embodiment of FIGS. 1-4, but with the pull up loops 40 at the top of the sleeve omitted. In their place (or in addition to) are finger access pockets 62, which are stitched to the sleeve exterior on three sides or mostly around its periphery of the pocket, leaving a finger accessible opening 64 on the fourth side facing the bottom of the sleeve. There is preferably one pocket on the lateral side and one on the medial side of the knee brace 60 near the top of the sleeve, and an optional pair at the bottom of the sleeve. The wearer of the knee brace 60 can insert his or her index or middle finger of each hand into the respective openings 64 and simultaneously pull upward thereby sliding the brace upward on the wearer's leg. At the bottom of the sleeve are an optional pair of pockets 66 on the medial and lateral sides, with upward facing finger openings 68. The wearer can insert his or her finger or thumb down into the openings 68 and push downward to slide the knee brace 60 downward on the leg. The pockets 64, 66 are generally, preferably aligned with the metal stiffeners 16, 18 and hinge 20 assembly at the medial and lateral sides of the knee brace. Thus, pulling on the pockets 64, 66 pulls the metal hardware assembly 16, 18, 20 along with the pockets to minimize chances of accidentally tearing the fabric or a seam. In yet another embodiment (not shown), the pockets 64, 66 may be replaced with low profile loops extending laterally from the sleeve surface. The loops provide finger or thumb access to hook on to for leverage to shift the knee brace up or down on the wearer's leg for improved fitment.

While particular forms of the invention have been illustrated and described, it will be apparent that various modifications can be made without departing from the spirit and scope of the invention. Furthermore, components from one embodiment may be modified or combined with the components from another embodiment.

What is claimed is:

1. An osteoarthritis knee brace for lifting a wearer's patella, comprising:
   a flexible and elastic sleeve having a tubular shape with an interior and exterior, lateral and medial surfaces, the sleeve further having a patella opening at an anterior surface, and a plurality of slits;
   a first pair of rigid longitudinal stiffeners pivoted therebetween at a hinge, disposed at the lateral surface of the sleeve;
   a second pair of rigid longitudinal stiffeners pivoted therebetween at a hinge, disposed at the medial surface of the sleeve;
   a flexible patella support having elongated strips at the ends thereof, wherein the patella support is positioned in the interior of the sleeve proximate with the patella opening, and wherein the elongated strips pass from the interior of the sleeve through the slits to the exterior of the sleeve, and further extend upward to be adjustably anchored to the sleeve, and wherein pulling upward on the elongated strips adjusts the patella support to lift the patella; and
   a strap extending circumferentially around the outside of the sleeve.

2. The osteoarthritis knee brace of claim 1, wherein the sleeve includes an anterior opening covered by a flap closure, and the anterior opening merges into the patella opening.

3. The osteoarthritis knee brace of claim 1, wherein the patella support includes a crescent shape and is elastic.

4. The osteoarthritis knee brace of claim 1, wherein a patella buttress including a gel material is disposed on the patella support.

5. The osteoarthritis knee brace of claim 1, wherein the knee brace includes internal condyle pads disposed inside the sleeve along the medial and lateral surfaces.

6. The osteoarthritis knee brace of claim 1, wherein the sleeve includes an upper anterior opening and a lower anterior opening.

7. The osteoarthritis knee brace of claim 6, wherein the upper anterior opening is covered by a flap closure, and the upper anterior opening merges into the patella opening, and wherein the lower anterior opening is covered by a flap closure, and the lower anterior opening merges into the patella opening.

8. The osteoarthritis knee brace of claim 1, wherein the patella support includes a tacky surface.

9. The osteoarthritis knee brace of claim 1, wherein flexible patella support is attached to the sleeve proximate to the bottom of the patella opening.

10. An osteoarthritis knee brace for lifting a wearer's patella, comprising:
    a sleeve having a tubular shape made from a flexible and elastic sheet with an interior and exterior, lateral and medial surfaces, the sleeve further having a patella opening at an anterior surface, and a plurality of slits;
    an upper anterior opening in the sleeve above the patella opening and a lower anterior opening in the sleeve below the patella opening, wherein the upper and lower anterior openings merge into the patella opening, and wherein the upper and lower anterior openings are closable by flaps;
    a first pair of rigid longitudinal stiffeners pivoted therebetween at a hinge, disposed at the lateral surface of the sleeve;
    a second pair of rigid longitudinal stiffeners pivoted therebetween at a hinge, disposed at the medial surface of the sleeve;
    a U-shaped patella support having elongated strips at the opposite ends thereof, wherein the patella support is anchored to the interior of the sleeve proximate with the patella opening, and wherein the elongated strips pass from the interior of the sleeve through the slits to the exterior of the sleeve, and further extend upward to be adjustably anchored to the sleeve, and wherein pulling upward on the elongated strips adjusts the patella support to lift the patella; and
    an upper strap extending circumferentially around the outside of the sleeve above the patella opening and a lower strap extending circumferentially around the outside of the sleeve beneath the patella opening.

11. The osteoarthritis knee brace of claim 10, wherein the first and second pairs of longitudinal stiffeners include flat metal bars.

12. The osteoarthritis knee brace of claim 10, wherein the sleeve includes external pockets that receive the first and second pairs of longitudinal stiffeners.

13. The osteoarthritis knee brace of claim 10, wherein the hinges of the first and second pairs of longitudinal stiffeners include hook and loop fasteners that attach to the exterior of the sleeve.

14. The osteoarthritis knee brace of claim 10, wherein the patella support further comprises a patella buttress made of gel.

15. An osteoarthritis knee brace for lifting a wearer's patella, comprising:
   a flexible and elastic sleeve having a tubular shape with an interior and exterior, lateral and medial surfaces, the sleeve further having an anterior opening along an entire length of the sleeve, the opening partially covered at an upper region and a lower region by flap closures and exposing a patella opening therebetween;
   a first pair of rigid longitudinal stiffeners pivoted therebetween at a hinge, disposed at the lateral surface of the sleeve;
   a second pair of rigid longitudinal stiffeners pivoted therebetween at a hinge, disposed at the medial surface of the sleeve;
   a patella support having elongated strips at the opposite ends thereof, wherein the patella support is anchored to the interior of the sleeve proximate with the patella opening, and wherein the elongated strips pass from the interior of the sleeve to the exterior of the sleeve, and further extend upward to be adjustably anchored to the sleeve, and wherein an upward pull on the elongated strips produces an upward directional force on the patella to lift the patella; and
   at least one strap extending circumferentially around the outside of the sleeve.

16. The osteoarthritis knee brace of claim 15, wherein the sleeve is formed from an elastic and flexible fabric sheet.

17. The osteoarthritis knee brace of claim 15, wherein the flap closures include hook and loop fasteners.

18. The osteoarthritis knee brace of claim 15, wherein flexible patella support is attached to the sleeve proximate to the bottom of the patella opening.

19. The osteoarthritis knee brace of claim 15, wherein flexible patella support is movable relative to the sleeve and is not attached to the sleeve at the bottom of the patella opening.

* * * * *